(12) United States Patent
Segura Rius et al.

(10) Patent No.: US 9,205,166 B2
(45) Date of Patent: Dec. 8, 2015

(54) APPARATUS FOR GENERATING HYDROXL RADICALS

(71) Applicant: Moving Sun Limited, London (GB)

(72) Inventors: Francisco J. Segura Rius, London (GB); Carl G. Hewett, London (GB); Abdelouahed Ezbiri, London (GB)

(73) Assignee: Moving Sun Limited, Milton Keynes (GB)

( * ) Notice: Subject to any disclaimer, the term of this patent is extended or adjusted under 35 U.S.C. 154(b) by 149 days.

(21) Appl. No.: 14/086,324

(22) Filed: Nov. 21, 2013

(65) Prior Publication Data

US 2014/0079597 A1  Mar. 20, 2014

Related U.S. Application Data

(63) Continuation of application No. 13/883,318, filed as application No. PCT/GB2011/001562 on Nov. 4, 2011, now abandoned.

(30) Foreign Application Priority Data

Nov. 4, 2010  (GB) .................................. 1018644.3

(51) Int. Cl.
*A61L 9/00* (2006.01)
*A61L 9/14* (2006.01)
*A61L 9/015* (2006.01)
*A61L 9/22* (2006.01)

(52) U.S. Cl.
CPC . *A61L 9/14* (2013.01); *A61L 9/015* (2013.01); *A61L 9/22* (2013.01); *A61L 2209/211* (2013.01); *A61L 2209/212* (2013.01)

(58) Field of Classification Search
CPC ................ A61L 9/00; A61L 9/20; A61L 9/03
USPC .................................................. 422/305–306
See application file for complete search history.

(56) References Cited

U.S. PATENT DOCUMENTS

| | | |
|---|---|---|
| 2006/0233683 A1 | 10/2006 | MacDonald |
| 2012/0020832 A1 | 1/2012 | St. Onge et al. |

FOREIGN PATENT DOCUMENTS

| | | |
|---|---|---|
| EP | 0529937 A2 | 3/1993 |
| GB | 1278043 A | 6/1972 |
| JP | 11226108 A | 8/1999 |

(Continued)

OTHER PUBLICATIONS

International Searching Authority, The International Search Report and the Written Opinion of the International Searching Authority, or the Declaration, PCT/GB2011/001562, May 14, 2012, 15 pgs.

*Primary Examiner* — Monzer R Chorbaji
(74) *Attorney, Agent, or Firm* — Wood, Herron & Evans, LLP (57) ABSTRACT

The invention provides a consumable cartridge for use in a hydroxyl radical generating apparatus, the consumable cartridge comprising: a reactant supply comprising a supply of a substance that reacts with ozone to form hydroxyl radicals; and an ozone supply comprising an ozone generator; wherein the ozone supply is fixed to the reactant supply. By supplying both a reactant supply and an ozone generator in the same consumable cartridge, maintenance operations on an associated base unit in a hydroxyl radical generating system can be minimized.

20 Claims, 10 Drawing Sheets

(56) References Cited

FOREIGN PATENT DOCUMENTS

| | | |
|---|---|---|
| JP | 2005237774 A | 9/2005 |
| KR | 100842355 B1 | 6/2008 |
| WO | 2005/026044 A2 | 3/2005 |
| WO | 2008/125879 A1 | 10/2008 |
| WO | 2010/117736 A2 | 10/2010 |
| WO | WO 2010/117736 A2 * 10/2010 | ................ A61L 9/22 |

* cited by examiner

APPARATUS FOR GENERATING HYDROXL RADICALS

CROSS REFERENCE TO RELATED APPLICATION

This is a continuation of U.S. patent application Ser. No. 13/883,318, filed, May 3, 2013 as the U.S. National Phase of International Application No. PCT/GB2011/001562, filed Nov. 4, 2011, which claims the benefit of UK Patent Application No. GB1018644.3, filed Nov. 4, 2010 and UK Patent Application No. GB1020392.5, filed Dec. 1, 2010, each of which is herein incorporated by reference in its entirety.

FIELD OF THE INVENTION

The present invention relates to an apparatus for producing hydroxyl radicals for delivery to an indoor environment. In particular, the invention relates to an apparatus comprising a consumable cartridge for use with a base unit, wherein the consumable cartridge and base unit operate together to provide and deliver hydroxyl radicals.

BACKGROUND OF THE INVENTION

The use of hydroxyl radicals as an airborne disinfectant in hospitals and other indoor environments is now becoming widespread. The disinfectant property of hydroxyl radicals has been known since the publication of research conducted in the 1960s at Porton Down in the UK and TNO in The Netherlands. Air based disinfection using hydroxyl radicals mimics a naturally occurring process in the outdoor environment, and so the concentration of hydroxyl radicals in the air is sometimes referred to as the "open air factor".

One example of an apparatus for generating hydroxyl radicals for airborne disinfectant is described in WO 2005/026044. A further apparatus is described in WO 2008/125879. The essential components of the apparatuses described in these documents are a supply of olefin, such as terpene, and a supply of ozone. An olefin vapour is produced from the supply of olefin and is mixed and reacts with the ozone to produce hydroxyl radicals.

While this basic chemistry for producing hydroxyl radicals is now well understood, there is a need to provide a convenient, safe and effective system for supplying hydroxyl radicals to an indoor environment. In particular, it would be desirable to provide a system that can be continuously and effectively operated by consumers with minimal interruption for maintenance and replenishment.

SUMMARY OF THE INVENTION

The present invention is defined in the appended independent claims, to which reference should be made. Preferred features of the invention are set out in the dependent claims.

In a first aspect, the invention provides a consumable cartridge for use in a hydroxyl radical generating apparatus, the consumable cartridge comprising: a reactant supply comprising a supply of a substance that reacts with ozone to produce hydroxyl radicals, and an ozone supply comprising an ozone generator; wherein the ozone supply is fixed to the reactant supply. By supplying both a reactant supply and an ozone generator in the same consumable cartridge, maintenance operations on an associated base unit in a hydroxyl radical generating system can be minimized.

The reactant supply is consumed and will become exhausted during use. It therefore needs to be replenished. The rate at which the reactant supply is used up depends on the pattern of usage of the apparatus and the size of the supply, but in view of a number of factors, including the physical size of the device, a reactant refill is typically designed to last a few months. In the system as described in WO 2008/125879, for example, olefin cartridges are replaced approximately every three months.

In prior apparatuses employing a base unit and refill cartridges, such as described in WO 2008/125879, an electronic ozone generator has been provided within the base unit together with the other electronic elements of the system. The base unit typically includes electronics for controlling a pump or fan to drive air through the base unit and power control electronics for providing the correct voltage to the ozone supply. However, the inventors have recognized that electronic ozone generators, although not consumable, also have a limited lifetime, particularly with continuous usage. The performance of an electric ozone generator, such as a corona discharge ozone generator, will degrade over time. An electric ozone generator might be expected to provide an acceptable level of performance for three or four months of continuous use. The other electronic elements of the system typically have a longer lifetime than the ozone generator, and accordingly it is the ozone generator that usually needs replacing first and most frequently from the electronic components.

Clearly, in environments such as hospitals and schools, it is vital to have disinfecting systems that are able to operate continuously and effectively, and any time in which the apparatus is out of service in order to replace faulty components is undesirable. By placing an ozone generator in the consumable cartridge, the ozone generator can be replaced at the same time as the reactant supply by an end user, and the need to call out technically trained service personnel to replace faulty or broken ozone generators can be avoided. The reactant supply and the ozone generator can be designed to have the same expected operating life.

Preferably, the ozone generator is an electrically powered ozone generator, such as corona discharge ozone generator or plasma ion generator. Other types of electrically powered ozone generator can be used, for example a cold plasma ozone generator, a UV type ozone generator, or a stainless steel filament in a dielectric tube. Preferably, the consumable cartridge includes at least one electrical contact configured to allow connection of an external power supply to the ozone generator.

Preferably, the consumable cartridge comprises an external housing, the reactant supply and the ozone supply being positioned within the external housing, wherein the electrical contact is accessible from an exterior of the external housing. The consumable cartridge may include a transformer and other electronic components. The transformer is used to provide the required voltage to the ozone generator, which is typically between 10 and 20 kV. Alternatively, the consumable cartridge may be configured for use with a base unit which contains an appropriate high voltage power source or a transformer for converting an external or battery supply voltage. As an alternative, the consumable cartridge may include a battery together with a suitable transformer. The reactant supply is preferably a reservoir containing the substance that reacts with ozone to produce hydroxyl radicals. The substance may be delivered from the reservoir by a capillary wick or membrane. The liquid may be vaporized by a flow of air past the wick or membrane. Additionally, a heater may be employed to aid vaporization.

The cartridge may comprise a first air inlet and a first outlet, wherein the first outlet is in fluid communication with the reactant in the reactant supply and the first inlet, and the cartridge may comprise a second air inlet and a second outlet, wherein the second outlet is in fluid communication with the ozone generator and the second air inlet.

Alternatively, the first air inlet and first air outlet may be defined by an associated base unit or by a combination of the consumable cartridge and the base unit, wherein the first outlet is in fluid communication with the reactant in the reactant supply and the first inlet. Similarly, the second air inlet and second air outlet may be defined by an associated base unit or by a combination of the consumable cartridge and the base unit, wherein the second outlet is in fluid communication with the ozone generator and the second air inlet.

The first outlet may be positioned adjacent the second outlet, and the cartridge (and/or base unit) may be configured so that air flow through one of the first outlet and the second outlet draws air through the other of the first outlet and the second outlet. This suction of air exploits the Venturi effect, which is a well understood effect in fluid dynamics.

The suction due to the Venturi effect can be controlled by appropriate geometry of the air flow conduits. For example, the consumable cartridge may define a first air conduit between the first air inlet and the first outlet that narrows between the first air inlet and the first outlet. Narrowing the conduit in this way increases the magnitude of the Venturi effect and so provides greater suction through the second outlet. Alternatively, or in addition, the consumable cartridge may define a second air conduit between the second air inlet and the second outlet, the second air conduit narrowing between the second air inlet and the second outlet. However, in practical devices, the required air flow past the reactant supply has been found to be so small that narrowing of the ozone conduit is often not necessary, and parallel sided conduits can be used.

The consumable cartridge or base unit may include a mixing chamber having a dispensing opening, the mixing chamber in fluid communication with both the first outlet and the second outlet, and configured to ensure a substantially complete reaction of vapors from the reactant supply with ozone from the ozone supply before release to the user environment through the dispensing opening.

The reactant supply may comprise a supply of olefin, such as D-Limonene, or may be a supply of another substance such as hydrogen peroxide. When the reactant is hydrogen peroxide the consumable cartridge or the base unit may advantageously further comprise an ion generator. The interaction of ions with ozone and hydrogen peroxide increases the yield of hydroxyl radicals and so reduces both the amount of ozone that needs to be generated and the amount of ozone that remains unreacted with the hydrogen peroxide.

The ion generator may be a separate device to the ozone generator and may be in the base unit or in the consumable cartridge, providing ions within the first or second air conduits. However, advantageously, the ion generator may be the same device as the ozone generator. In this case, the ozone generator may be a plasma ion generator.

The ion generator is also preferably configured to ionize air at a relatively low voltage in order to avoid excessive ozone generation and nitric oxide generation. To achieve this, one of the electrodes in the ion generator may be configured with a plurality of fine spikes. This produces a high potential gradient around the spikes, increasing ionization for a given applied voltage when compared to electrode designs producing smaller potential gradients. The ion generator is preferably configured to generate negative ions, as this reduces ozone generation and nitric oxide generation compared with positive ions.

In a second aspect, the invention provides an apparatus for generating hydroxyl radicals comprising a base unit and a consumable cartridge, the consumable cartridge being in accordance with the first aspect of the invention, and the base unit comprising a means for providing electrical power to the consumable cartridge, and a means for driving air through the apparatus. The base unit may comprise a transformer for transforming a mains voltage or other external supply voltage to a voltage suitable for the ozone generator in the consumable cartridge. The base unit may comprise a mixing chamber in fluid communication with an outlet in fluid communication with the reactant supply and an outlet in fluid communication with the ozone supply, the mixing chamber further comprising a dispensing outlet.

The base unit may comprise a base unit air inlet and base unit air conduit between the base unit air inlet and an air inlet on the consumable cartridge, or partially defined by the consumable cartridge, wherein the inlet conduit narrows between the base unit air inlet and the air inlet on, or partially defined by, the consumable cartridge. The narrowing of the inlet conduit accelerates the air flow towards the air inlet on, or partially defined by, the consumable cartridge. The speed of the air flow past the ozone generator affects the concentration of ozone in the air supplied to the mixing chamber. The narrowing of the inlet conduit can therefore be designed to provide a predetermined ozone concentration. Other ways to control ozone and olefin concentration include controlling the speed of a pump or blower used as the means for driving air through the apparatus, and controlling the voltage supplied to the ozone generator.

The base unit may comprise an ion generator within or adjacent the base unit air conduit. The ion generator is also preferably configured to ionize air at a relatively low voltage in order to avoid excessive ozone generation and nitric oxide generation. To achieve this, electrodes in the ion generator may be configured as a plurality of fine spikes. This produces a high potential gradient around the spikes, increasing ionization for a given applied voltage when compared to electrode designs producing smaller potential gradients. The ion generator is preferably configured to generate negative ions, again to reduce ozone generation and nitric oxide generation.

In a third aspect, the invention provides a base unit for producing hydroxyl radicals, the base unit suitable for use with a consumable cartridge in accordance with the first aspect of the invention and a means for connection with a power supply, a base unit air inlet, a means for moving air through the consumable cartridge, and a socket configured to receive the consumable cartridge, the socket including electrical contacts suitable for supplying electrical power from the means for connection with a power supply to the consumable cartridge.

The base unit may comprise a base unit air conduit between the base unit air inlet and an air inlet on, or partially defined by, the consumable cartridge, wherein the base unit air inlet conduit narrows between the base unit air inlet and air inlet on, or partially defined by, the consumable cartridge. The narrowing of the air inlet conduit accelerates the air flow to the air inlet on the consumable cartridge.

The base unit may comprise an ion generator within or adjacent the base unit air conduit. The ion generator is also preferably configured to ionize air at a relatively low voltage in order to avoid excessive ozone generation and nitric oxide generation. To achieve this, electrodes in the ion generator may be configured as a plurality of fine spikes. This produces a high potential gradient around the spikes, increasing ionization for a given applied voltage when compared to electrode designs producing smaller potential gradients. The ion generator is preferably configured to generate negative ions, again to reduce ozone generation and nitric oxide generation.

In a fourth aspect, the invention provides a hydroxyl radical generating apparatus, comprising:

at least one air inlet and a dispensing outlet, and an air flow path between the air inlet and the dispensing outlet;

a supply of hydrogen peroxide configured to supply hydrogen peroxide into the air flow path;

a supply of ozone configured to supply ozone into the air flow path; and an ionizer configured to generate and supply ions into the air flow path.

The apparatus may comprise a first air inlet and a second air inlet. The apparatus may further comprise a mixing chamber, the mixing chamber in fluid communication with the first and second air inlets and the dispensing outlet. The supply of hydrogen peroxide may be positioned between the first air inlet and the mixing chamber. The supply of ozone may be positioned between the second air inlet and the dispensing outlet. The supply of hydrogen peroxide may be provided in one or more cartridges. The supply of ozone may also be provided in one or more cartridges, which may be the same as or different to cartridge(s) containing the supply of hydrogen peroxide.

The apparatus may comprise a first outlet, wherein the first outlet is in fluid communication with the hydrogen peroxide supply and the first inlet, and a second outlet, wherein the second outlet is in fluid communication with the ozone generator and the second air inlet. The first outlet may be positioned adjacent the second outlet, and the apparatus may be configured so that air flow through one of the first outlet and the second outlet draws air through the other of the first outlet and the second outlet. This suction of air exploits the Venturi effect, which is a well understood effect in fluid dynamics. The first and second outlets may open into the mixing chamber.

The suction due to the Venturi effect can be controlled by appropriate geometry of the air flow conduits. For example, the apparatus may define a first air conduit between the first air inlet and the first outlet that narrows between the first air inlet and the first outlet. Narrowing the conduit in this way increases the magnitude of the Venturi effect and so provides greater suction through the second outlet. Alternatively, or in addition, the apparatus may define a second air conduit between the second air inlet and the second outlet, the second air conduit narrowing between the second air inlet and the second outlet.

A means to drive air through the air flow path may be provided, such as a fan, pump or blower. The means to drive air may be provided between the second air inlet and the mixing chamber, between the first air inlet and the mixing chamber or between the mixing chamber and the air outlet. More than one means to drive air through the apparatus may be provided, in different locations.

The ozone supply may be an ozone generator. Preferably, the ozone generator is an electrically powered ozone generator. Most preferably, the ozone generator also acts as the ionizer. An example of a suitable ozone generator is a corona discharge ozone generator or plasma ion generator. Other types of electrically powered. ozone generator can be used, for example a cold. plasma ozone generator, a UV type ozone generator, or a stainless steel filament in a dielectric tube.

If an ionizer is provided as a separate element to the ozone generator, any suitable ionizer may be used.

The apparatus may include a transformer and other electronic components. The transformer is used to provide the required voltage to the ozone generator, which is typically between 10 and 20 kV. The hydrogen peroxide supply preferably comprises a liquid reservoir within a consumable cartridge. The hydrogen peroxide may be delivered from the reservoir by a capillary wick or membrane. The liquid may be vaporized by a flow of air past the wick or membrane. Additionally, a heater may be employed to aid vaporization.

The apparatus may further comprise a scent supply, configured to supply a chemical having a scent into the air flow path.

In a fifth aspect, there is provided a method of producing hydroxyl radicals, comprising:

providing hydrogen peroxide into an air flow path;
providing ozone into the air flow path;
providing ions into the air flow path; and
mixing the hydrogen peroxide, ozone and ions to produce hydroxyl radicals.

The method may further comprise releasing the hydroxyl radicals from the air flow path into an external environment.

BRIEF DESCRIPTION OF THE DRAWINGS

Embodiments of the present invention will now be described in detail, by way of example only, with reference to the accompanying drawings, in which.

DETAILED DESCRIPTION OF THE INVENTION

Figure 1A:
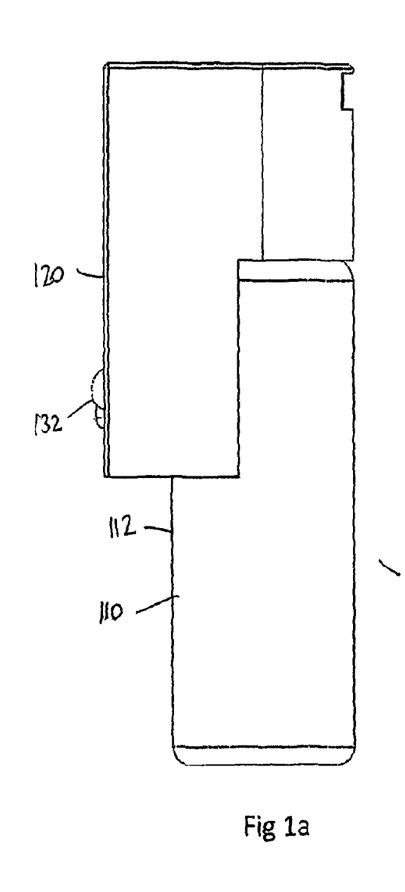
FIGS. 1a, 1b and 1c illustrate a consumable cartridge in accordance with a first embodiment of the invention.
Figure 1B:
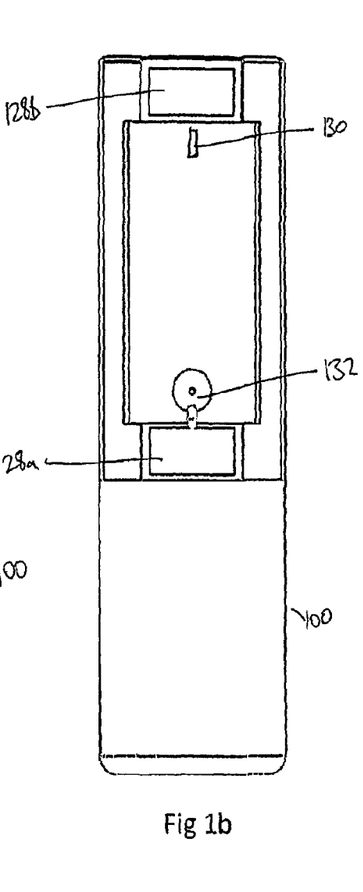
Figure 1C:
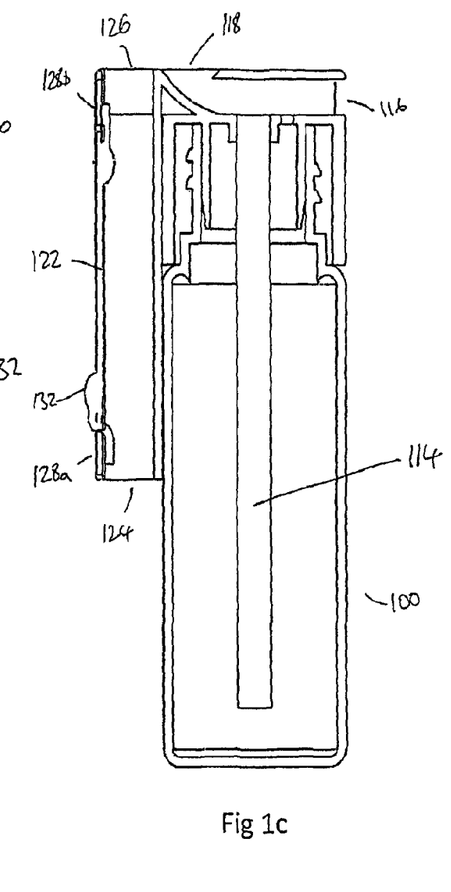

FIGS. 1a, 1b and 1c illustrate a consumable cartridge in accordance with a first embodiment of the invention. FIG. 1a is a side view of the cartridge, FIG. 1b is an end view of the cartridge and FIG. 1c is a cross-sectional view of the cartridge. The cartridge boo comprises an olefin supply no and an ozone generator 120. The olefin supply comprises a container 112 in which an amount of liquid olefin, such as terpene, is stored. A wick 114 is inserted in the container and extends out of a top end of the container for delivery of olefin to an olefin outlet. This is illustrated most clearly in FIG. 1c which shows the wick extending from within the container to a conduit. extending between air inlet 116 and an outlet 118. Air entering the inlet 116 passes over the wick 114 and picks up an olefin vapour as it does so, before exiting through outlet 118. The wick 114 may be formed from any suitable fibrous material, such as polypropylene fibre.

The reactant in this example is an olefin or mixture of olefins. However, other substances that react with ozone to produce hydroxyl radicals may be used, for example, hydrogen peroxide or cinnamaldehyde.

It should also be noted that the reactant supply need not be in liquid form and might be solid or gaseous instead. For example, solid beeswax may be used as an olefin source. Also, the wick illustrated in FIGS. 1a, 1b and 1c may be replaced by other means of conveying reactant vapour to an air flow. For example, a vapour permeable membrane may be used to separate the reactant supply from the associated air flow. The ozone supply 120 comprises an electronic ozone generator 122 located adjacent an air passage having an inlet 124 and an outlet 126. Oxygen in the air entering through inlet passage 124 passes over the ozone generator, which in this example is a corona discharge device, and ozone is thereby formed. The ozone rich air exits through outlet 126. Suitable corona discharge ozone generators, such as plasma ion generators, are available from Trump Electronics of East Yongfu Road, Tianchang, China 201100 (www.trumpxp.com) and may be formed from aluminum oxide or calcium silicate for example. Alternative forms of ozone generator may also be used, such as UV type ozone generators, cold plasma ozone generators or a stainless steel filament in a dielectric tube.

In order to provide the necessary voltage to the ozone generator 122, electrical contacts 128a and 128b are provided on a back surface of the ozone generator. The outlets 118 and 126 are immediately adjacent one another within a unitary molding which defines the conduits though which the air passes. The arrangement shown in FIG. 1c, with the outlets immediately adjacent one another, is configured such that an air flow past the ozone generator and out of outlet 126, draws air through inlet 116 past the olefin wick and out of outlet 118. The flow of air past the olefin supply is a result of the Venturi effect, which is a well-understood effect in fluid dynamics. The air flow exiting outlet 126 causes a reduction in pressure in the region of outlet 126, which pulls air through inlet 116. This is illustrated more clearly in FIG. 3. The molding defining the air inlets and outlets of the ozone supply and the olefin supply can be connected to the container 112 using a screw fitting or push fitting.

The electrical contacts 128a and 128b are formed from any suitable conducting material, such as copper, and are spaced apart to avoid arcing. Corona discharge ozone generators operate at very high voltages so that arcing is possible problem if the electrical contacts are placed too close together.

Figure 2A:
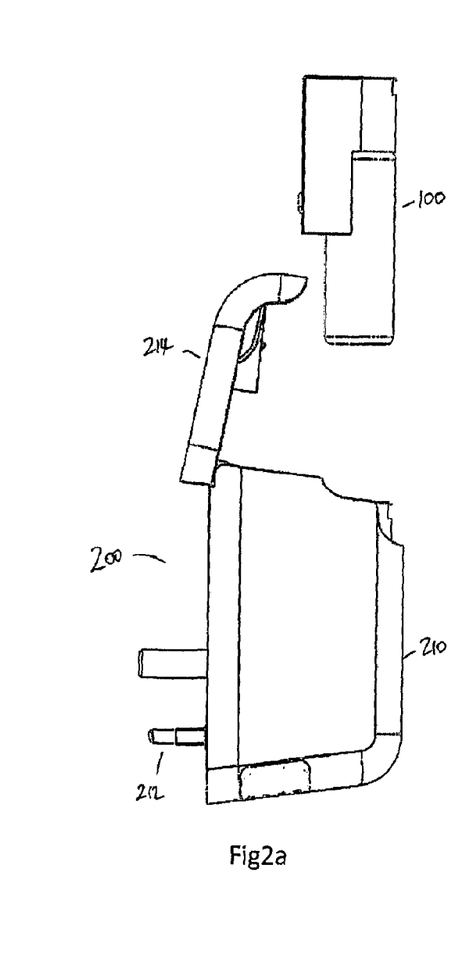
FIGS. 2a, 2b and 2c illustrate the consumable cartridge of FIG. 1 in combination with a base unit in accordance with the invention.
Figure 2B:
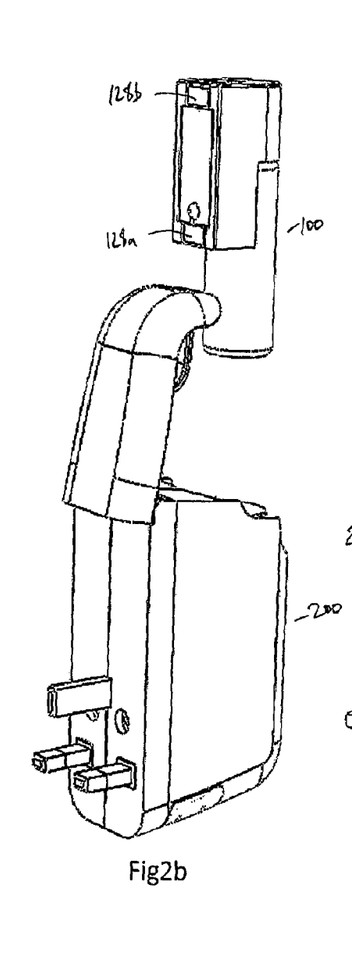
Figure 2C:
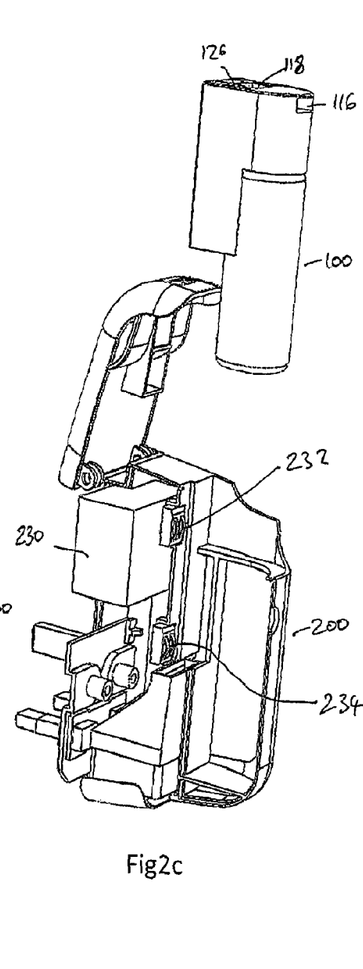

FIGS. 2a, 2b and 2c illustrate the cartridge shown in FIGS. 1a, 1b and 1c, and its relationship with a base unit which is configured to connect directly to a mains power supply. FIG. 2a is a side view, FIG. 2b is a perspective view and FIG. 2c is a cut-away view with an element of the base unit housing removed. The base unit 200 comprises a housing 210 and a hinged lid section 214, together with a standard bayonet-type plug for connection to a mains power supply. The hinged lid 214 is shown in an open position to allow for insertion or removal of the cartridge 100. As shown in FIG. 2c, within the base unit there are electronic components 230 including a transformer which is used to transform the mains supply voltage to the high voltage required for the ozone generator in the cartridge. Electrical contacts 232 and 234 are provided for contact with corresponding contacts 128a and 128b on the cartridge. The electrical contacts 232, 234 in the base unit are spring loaded to ensure good electrical contact.

Figure 3:
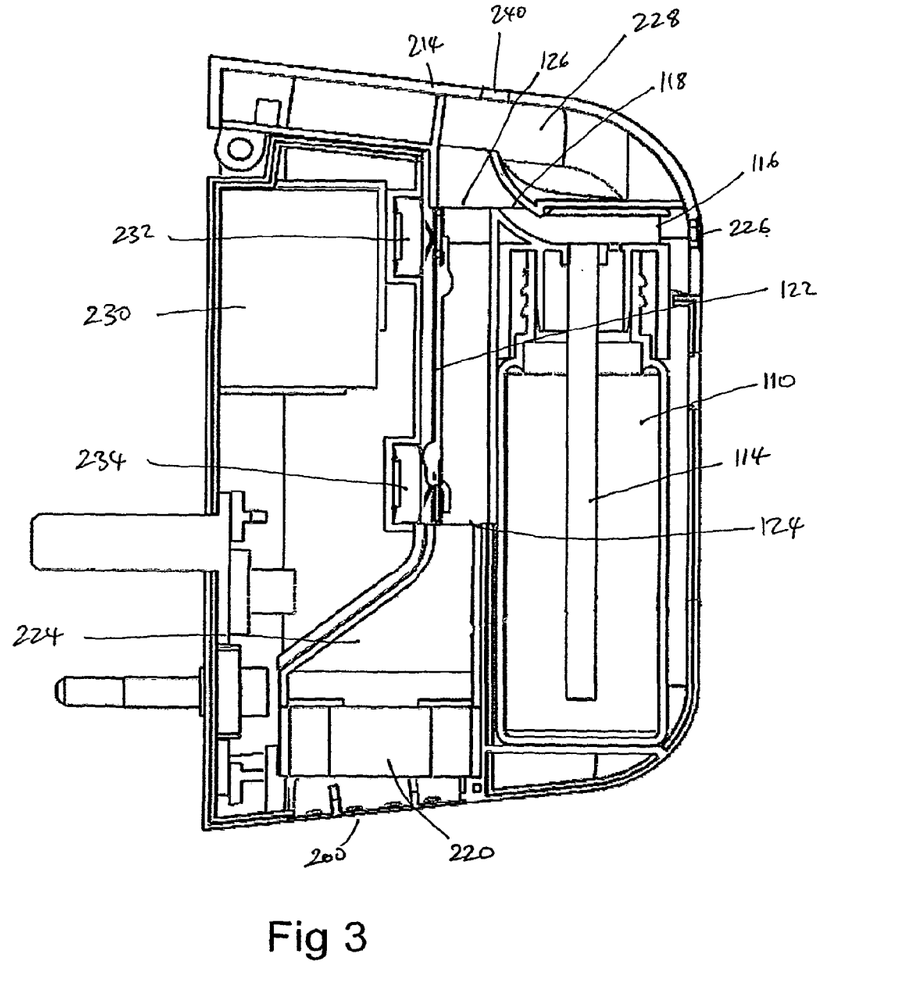
FIG. 3 is a cross-sectional view of the consumable cartridge of FIG. 1 installed in the base unit shown in FIG. 2.

FIG. 3 is a cross-section of the base unit of FIGS. 2a to 2c together with the cartridge, with the cartridge installed within the base unit. The base unit includes a fan 220 which draws air in through air inlet 222 up into a narrowing air conduit 224 which connects to inlet 124 on the cartridge. Air drawn in by the fan is accelerated as the conduit narrows. The accelerated air flow then passes over the ozone generator 122 in the cartridge and out of outlet 126 into mixing chamber 228 formed within the lid 214 of the base unit. The reduced pressure of the air flowing out through outlet 126 draws air in through inlet 226 in the lid 214 through inlet 116 in the cartridge and over the wick 114 containing the olefin, in this case terpene. The olefin rich air then exits through outlet 118 into mixing chamber 228 where it mixes with and reacts with the ozone to form hydroxyl radicals. The hydroxyl radicals then leave the mixing chamber through dispensing outlet 240.

The apparatus may be designed for different airflow. For example the fan may be provided in the conduit with the wick 114 and the internal geometry of the base unit and cartridge configured to use the Venturi effect to suck air through the ozone generator. Equally the narrowing of the air flow conduits may be provided in the cartridge instead of or as well as in the base unit. Furthermore, the Venturi effect may be exploited within the base unit rather than at the outlets of the cartridge. For example, the base unit may include output conduits that match the position of the outlets on the consumable cartridge and act as continuations of the air flow passages formed in the cartridge. These output conduits may debouche into a mixing chamber, and the Venturi effect at that point may cause air to be sucked through the conduit in contact with the olefin supply.

Alternatively, the ozone generator and olefin supply may be placed in the same conduit, one after the other in the direct of air flow, or substantially opposite each other within the same conduit. However, this is not the preferred option because residues resulting from olefin vapour and the products of reactions with ozone may build up on the ozone generator or on the olefin wick or membrane. This reduces the performance of the system, and so having separate conduits for the olefin supply and the ozone supply so that they mix and react in a downstream location is preferable.

FIG. 3 also shows the position of the transformer and associated electronics 230 that supplies a high voltage to contacts 234 and 232, which are shown in contact with electrical contacts 128a and 128b on the consumable cartridge. Electrical connection of the mains power supply to the electronics 230 is not shown, but is provided by suitable wiring components.

The mixing chamber 228 formed within the lid 2 includes a dispensing outlet 240 through which hydroxyl radicals pass to the user environment. The mixing chamber may have a complex geometry in order to ensure that the ozone rich air from outlet 126 and olefin rich air from outlet 118 have sufficient time, and are sufficiently turbulent to provide complete mixing. WO 2008/125879 describes a mixing chamber for this purpose, and the same or a similar geometry can be used in the embodiment shown in FIG. 3.

The combination of base unit and cartridge shown in FIG. 3 can be configured to operate continuously or may include control electronics that provide power to the fan and the ozone generator intermittently so that hydroxyl radicals are released into the atmosphere on an intermittent or periodic basis. A user interface may be included on the base unit to allow a user to program the mode of operation of the device so that hydroxyl radicals are only provided during times when users are in the immediate vicinity. This might be useful, for example in a school environment. An electronic timer or cycle counter may also be provided together with an audible or visible alarm to alert the user when a cartridge requires replacement.

The first embodiment can also be implemented using hydrogen peroxide as the reactant, instead of (or in addition to) olefin. When using hydrogen peroxide, there is a particular benefit to the generation of ions within the air flow through the device, as is explained with reference to FIG. 9. An ion generator may be included in the base unit or in the consumable cartridge, but in the first embodiment the ozone generator also functions as an ion generator. The use of a plasma ion generator to produce ozone and to ionize air is both effective and economical.

It is desirable to produce ions at the lowest possible voltage level with the ozone generator in order to keep the production of ozone low and to minimize the production of any nitric oxide. In order to achieve this, the electrodes within the plasma ion generator comprise a plurality of sharp spikes. The sharp spikes produce a large potential gradient within the ozone generator increasing the likelihood of ionization for a given applied voltage. The plasma ion generator is also configured to produce negative ions, again to keep ozone production within desirable levels. A suitable plasma ion generator to this design is available from Trump Electronics, referenced above.

Figure 4A:
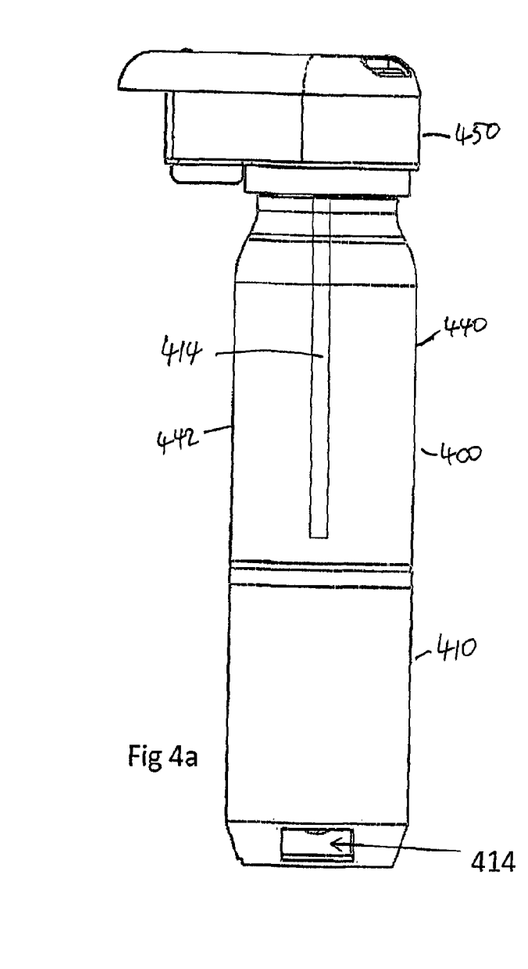
FIGS. 4a and 4b illustrate a consumable cartridge in accordance with the second embodiment of the present invention.
Figure 4B:
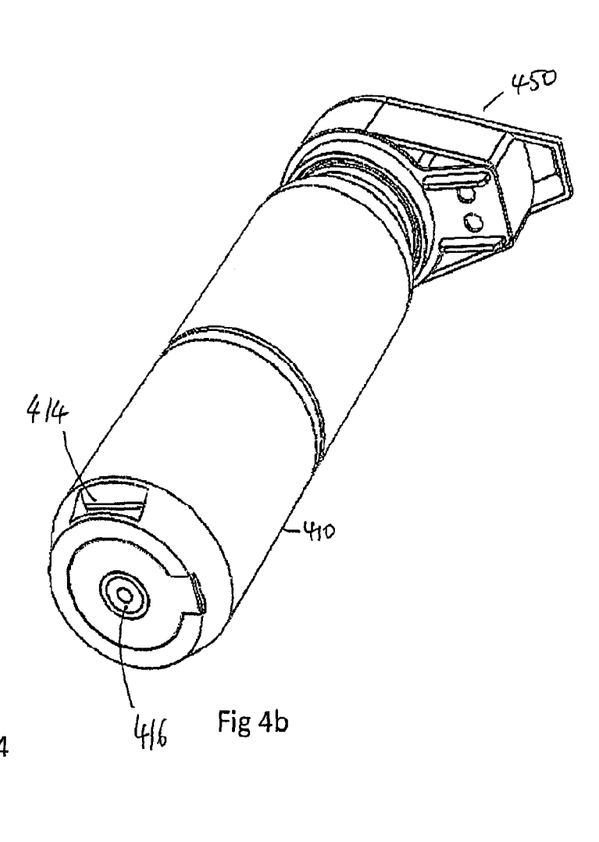

FIGS. 4a and 4b show a second embodiment of a consumable cartridge in accordance with the invention. FIG. 4a is a side view and FIG. 4b is a perspective view from the underside. The cartridge shown in FIG. 4a includes not only an ozone generator, but also the transformer required to convert an external supply voltage to the voltage required by the ozone generator. Referring now to FIG. 4a, the consumable cartridge 400 of the second embodiment comprises an ozone supply 410, an olefin supply 440 and a dosing head 450 in which olefin rich air and ozone rich air is mixed in order to generate hydroxyl radicals. FIG. 4b shows an electrical contact pad 416 on the underside of cartridge 400 for connection to a power supply in the base unit.

As in the first embodiment, the reactant supply (again in this example an olefin supply) consists of a container 442 within which a wick 444 is placed. Olefins within the container are drawn into the wick and can be extracted from an open end of the wick as a vapour. As with the previous embodiment, it should be clear that a solid or gaseous reactant source may be used instead of a liquid source, and that a membrane may be used in place of a wick.

Figure 5:
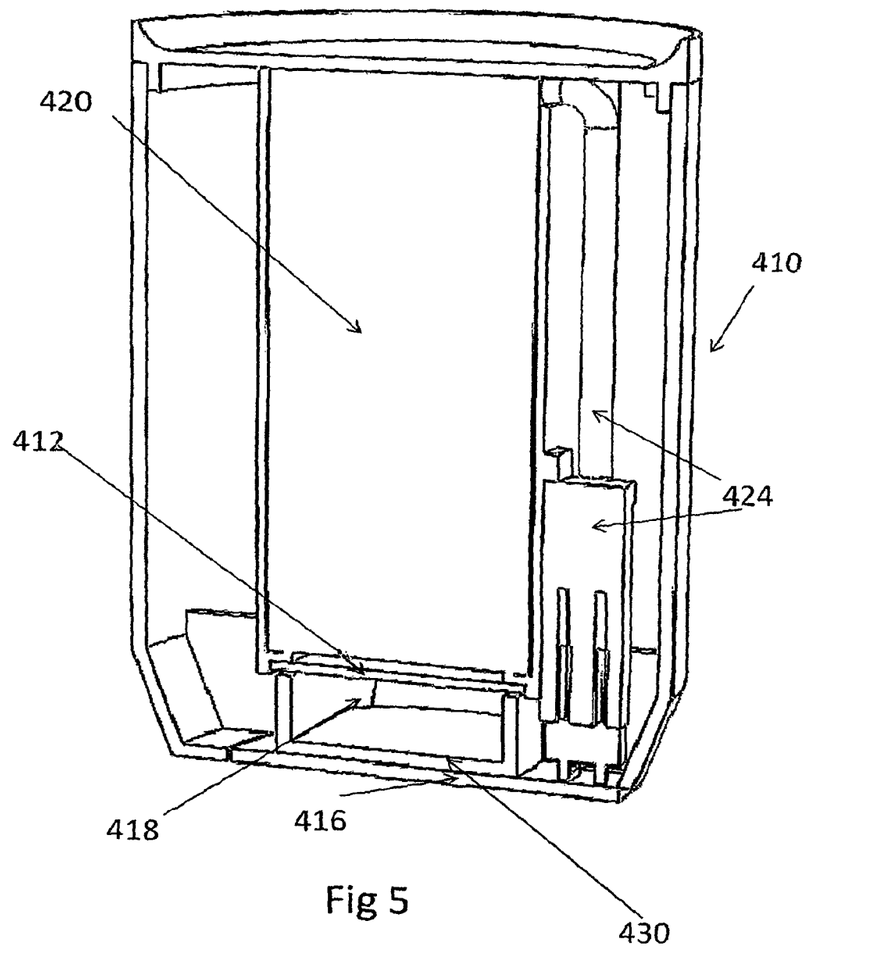
FIG. 5 illustrates the ozone generator module of the cartridge shown in FIGS. 4a and 4b.

In this embodiment the ozone supply is provided underneath the olefin supply and is shaped so that the cartridge is substantially cylindrical. Alternative relative positioning of the olefin supply and the ozone generator is equally possible with alternative configurations of the air conduits used to supply olefin rich air and ozone rich air to the mixing chamber in the dosing head. The configuration of the ozone supply is shown in more detail in FIG. 5. The ozone generator 412 is provided as a downward facing component to which a suitable transformer 420 is connected. The transformer is connected to an external electric contact pad 416 formed on a dual sided printed circuit board by wiring 424 extending within the housing of the ozone supply. A component 430 is provided in order to separate the air conduit 418 in which ozone rich air is generated from the electrical contact pad 416 and the associated electronics 420. This is important to prevent oxidation of the electronic components. Component 430 may be integral with the housing of the consumable cartridge or may be provided as a separate component. Air enters the ozone supply through inlet 414 and exits through a similar outlet on the opposite side of the housing. This flow of air not only provides oxygen from which ozone is generated, but also provides some cooling for the electronics, and in particular for the transformer.

Figure 6:
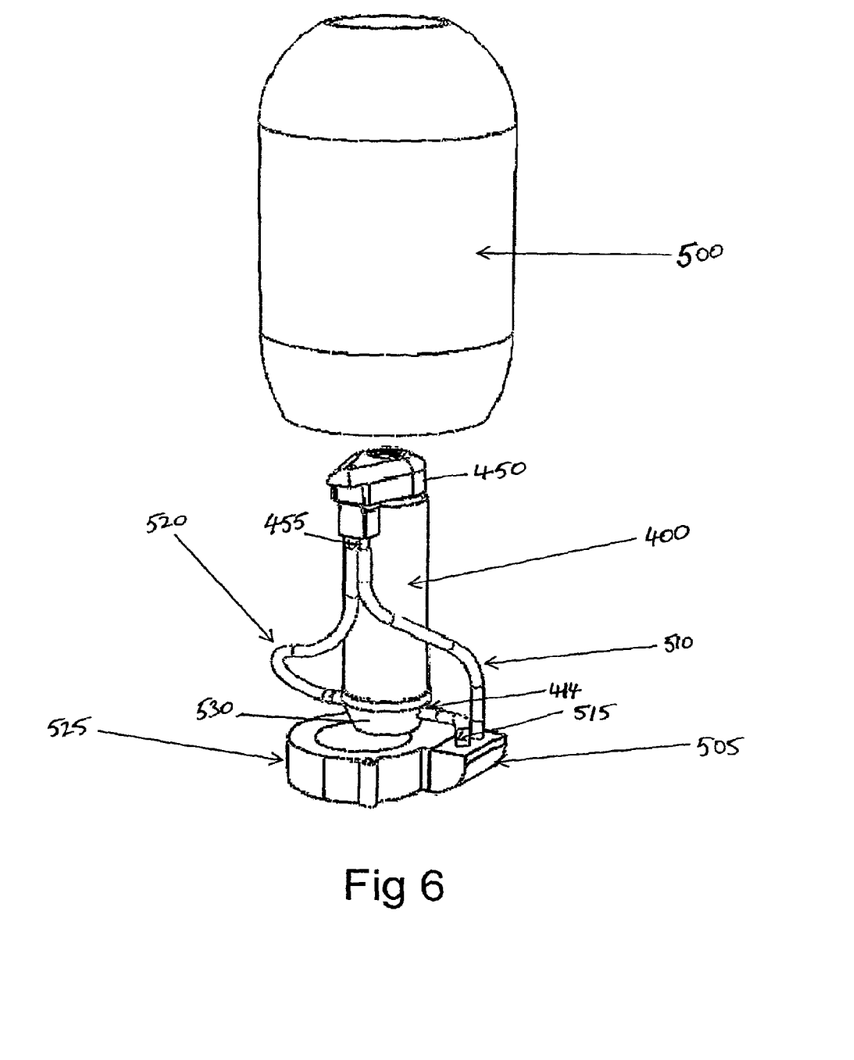
FIG. 6 illustrates the consumable cartridge of the second embodiment installed in a base unit, with the casing in a removed position.

FIG. 6 shows the consumable cartridge 400 installed within a base unit, with the casing 500 of the base unit shown removed above the cartridge. The cartridge 400 is inserted through an opening (not shown) formed in the top of the casing 500 and engages both with air flow hoses and with an electrical contact pad in the base unit.

The base unit includes an air inlet 505 through which air from the external environment can enter the base unit through the casing 500. The base unit air inlet 505 is in fluid communication with hoses 510 and 515 which are connected to the olefin supply and ozone generator respectively. A further hose 520 connects an output of the ozone generator to the dosing head 450. Within the dosing head the ozone rich air and olefin rich air streams are mixed before being exhausted to the external environment. A fan or pump 525 is provided in the base unit to move air from the base unit air inlet 505 through the hoses 510 and 515.

The dosing head 450 on the consumable cartridge includes sockets which mate with connectors provided on the end of hoses 510 and 520 when the cartridge is inserted in the base unit. The bottom of the cartridge, containing the ozone generator engages with a sealing skirt 530 in the base unit, as shown in FIG. 7.

Figure 7:
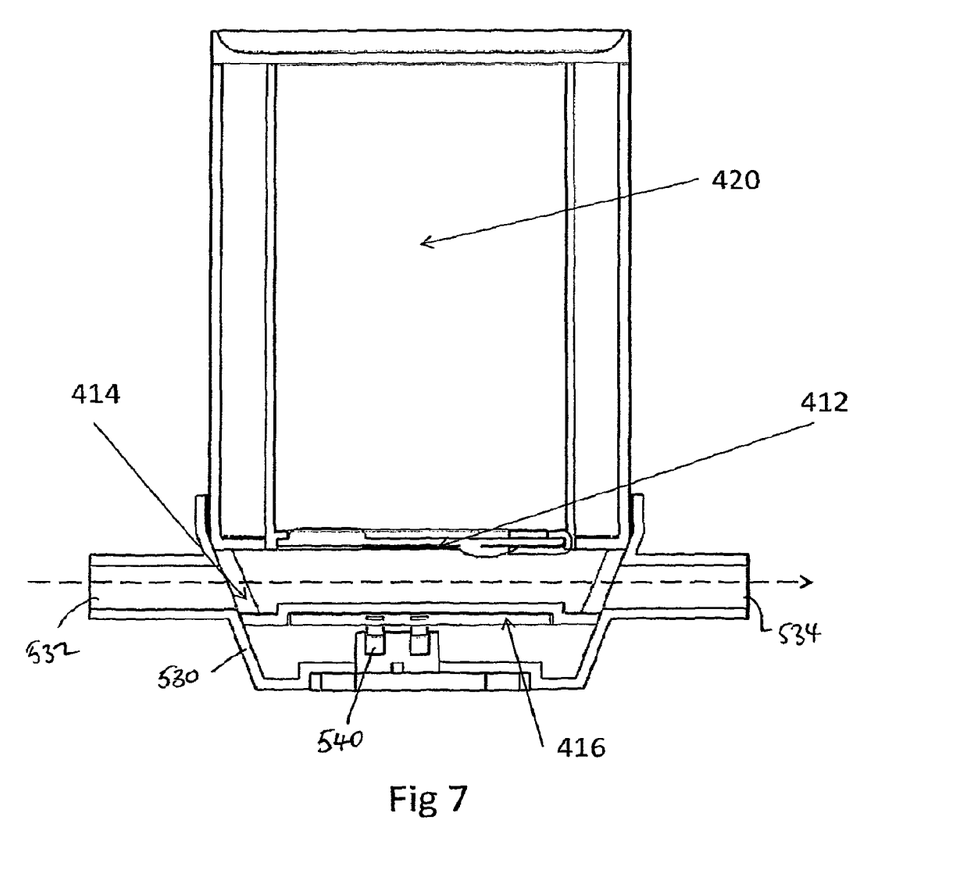
FIG. 7 illustrates the flow path of air through the ozone generator shown in FIGS. 5 and 6.

FIG. 7 shows the flow path of the air through the ozone generator in more detail, and in particular shows the sealing skirt 530 which engages with the bottom of the cartridge to provide both electrical power and a sealed air flow passage from hose 515 past the ozone generator to hose 520. The sealing skirt 530 is tapered to engage the tapered end of the cartridge 400, and includes an inlet opening 532 and an outlet opening 534, which are connected to hoses 515 and 520 respectively. The inlet and outlet openings provide a sealed connection to the inlet and outlet of the ozone generator. The skirt also includes an electrical contact 540 that engages with contact 416 formed on the cartridge when the cartridge is positioned within the sealing skirt 530, for providing power to electronics 420 within the cartridge.

Figure 8:
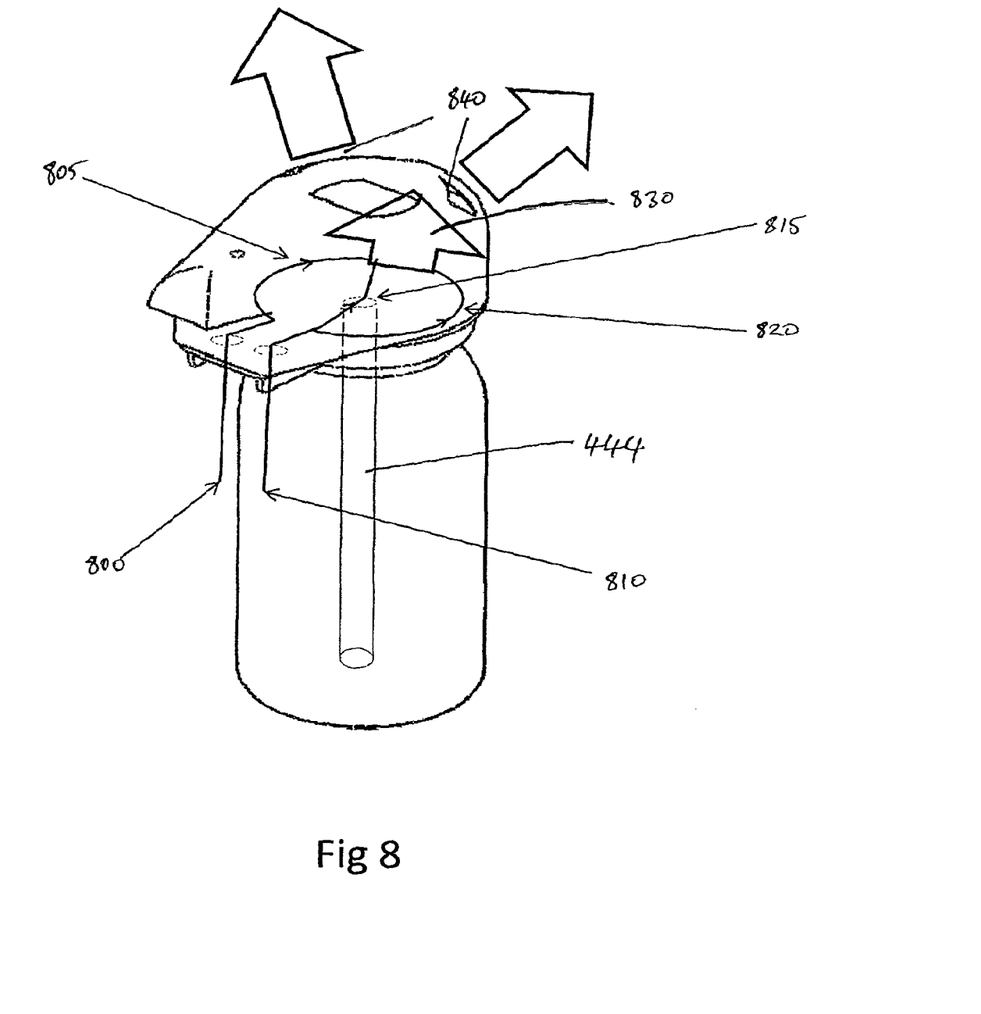
FIG. 8 is a perspective view of the dosing head shown in FIG. 4.

FIG. 6 does not show the further electrical components within the base unit, but the electronics can be placed anywhere within the casing 500 and connect to contact 46 on the cartridge through the sealing skirt. FIG. 8 is a schematic perspective view of the dosing head 450, showing the flow paths through the dosing head 450 to the dispensing outlets 840. The ozone rich air from the ozone generator is shown as line 800. The air stream from hose 510 for the olefin supply is shown as line 810. The ozone rich air entering the dosing head is circulated along path 805 to mixing chamber 830. The air for the olefin supply is split in the dosing head, with some of the air passing over wick 444 along path 815 to extract olefin vapour and some of the air passing through an air bypass flow path 820 that bypasses the wick. Both flow paths 815 and 820 meet at mixing chamber 830 together with the ozone rich air. The ozone and olefins react in mixing chamber 830 to produce hydroxyl radicals, which are then released into the environment through dispensing outlets 840. The dosing head 450 is formed from molded plastic component. A more detailed description of the dosing head shown in FIG. 8 can be found in WO2008/125879, the contents of which are incorporated by reference. The dosing head provides a mixing chamber downstream of the olefin supply and the ozone generator and ensures that substantially all of the ozone from the ozone generator is reacted with olefin molecules. This ensures both safe levels of ozone in the environment and high levels of hydroxyl radicals. The base unit can be designed to accommodate other configurations of consumable cartridge. For example, if the ozone generator and olefin supply are arranged side by side in the insertion direction of the cartridge into the base unit, the hoses and sealing skirt could be redesigned to provide the necessary fluid flow paths and electrical connection without changing the principle of operation.

Figure 9:
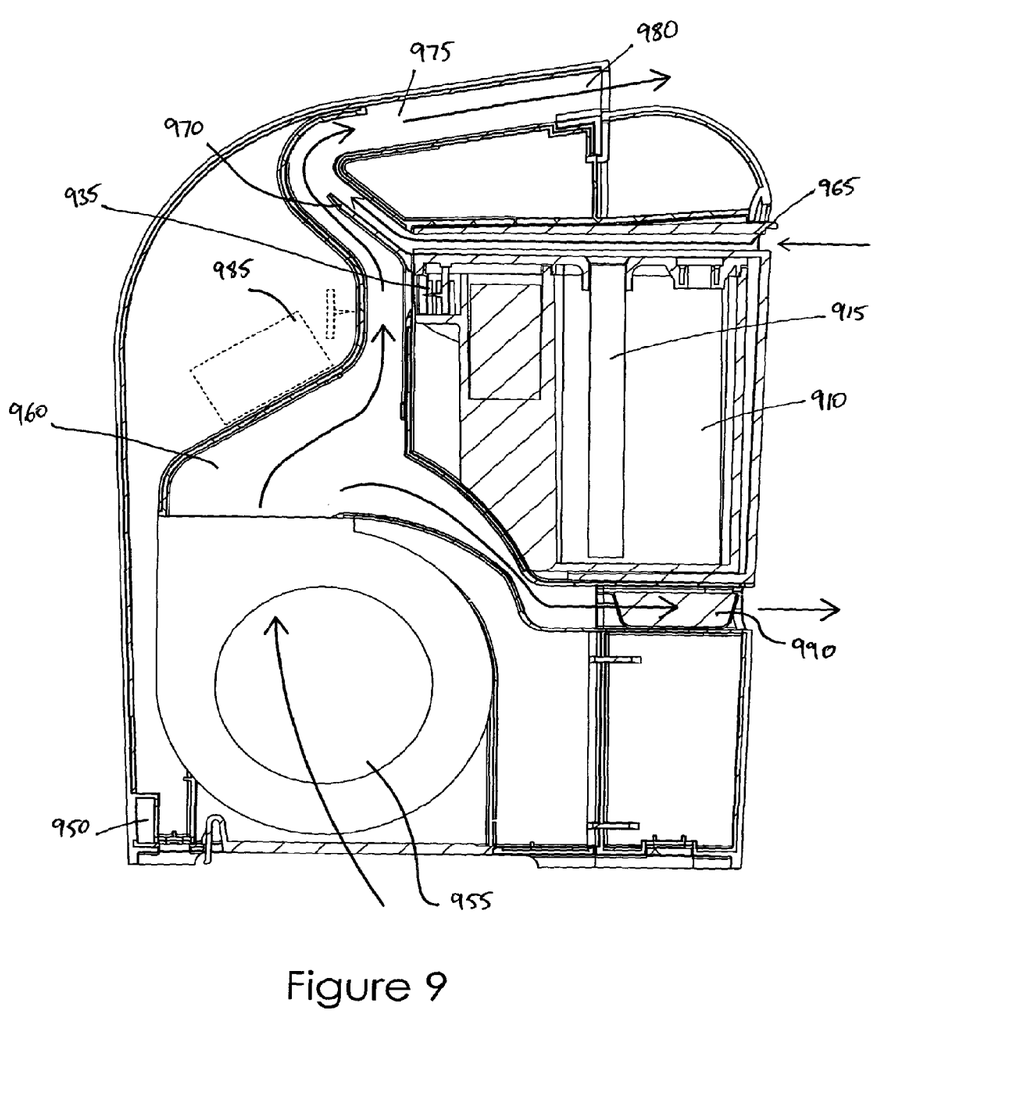
FIG. 9 is a cross-sectional view of an apparatus in accordance with a third embodiment of the invention.
Figure 10A:
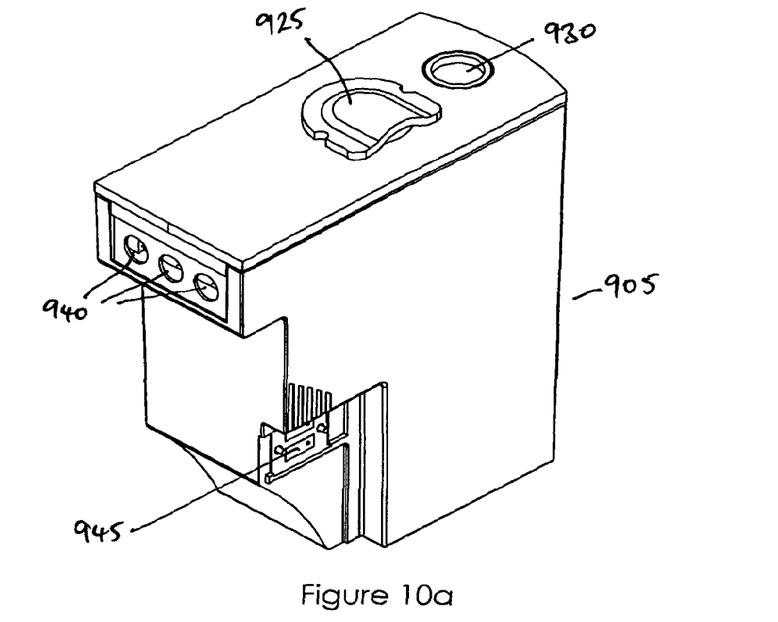
FIGS. 10a and 10b are a perspective view and a cross-sectional view of a cartridge for use in the apparatus of FIG. 9.
Figure 10B:
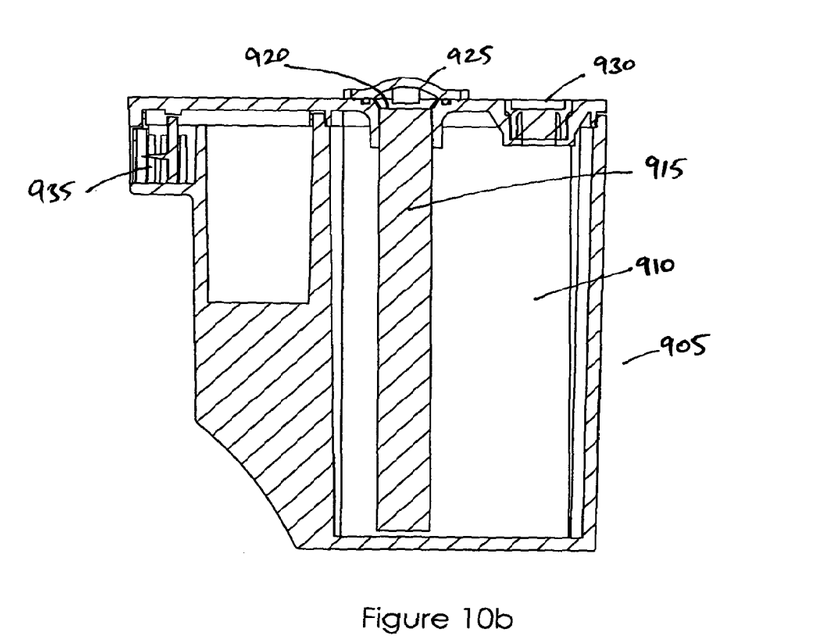

FIGS. 9, 10 and 10a illustrate an alternative design of base unit and cartridge. FIG. 9 is a cross-sectional view. The base unit 900 is configured to receive a cartridge 905. The cartridge is illustrated in more detail in FIGS. 10a and 10b.

The apparatus shown in FIG. 9 uses hydrogen peroxide as the reactant. Liquid hydrogen peroxide is contained in a reservoir 910 in the cartridge 905. A wick 915 (not shown in FIG. 9) is inserted in the reservoir and extends out of a top end of the cartridge for delivery of hydrogen peroxide to an outlet 920. This is illustrated most clearly in FIG. 10b which shows the wick extending from within the reservoir to the exterior of the cartridge. The wick is covered by a removable cap 925, which is placed over the opening 920 and protects the wick and prevents spillage. The cap 925 is removed by the user before inserting the cartridge into the base unit. A filling aperture 930 is also shown, through which the reservoir is filled with hydrogen peroxide. It is covered with a breathable cap to prevent liquid spillage, but to allow for the escape of gas. The wick 915 may be formed from any suitable fibrous material, such as polypropylene fibre. An ozone generator 935 is provided in the cartridge. The ozone generator is a corona discharge ozone generator that generates ions as well as ozone in operation. Suitable corona discharge ozone generators, such as plasma ion generators, are available from Trump Electronics of East Yongfu Road, Tianchang, China 201100 (www.trumpxp.com) and may be formed from aluminum oxide or calcium silicate for example. The ozone generator comprises a series of openings 940 that allow air to pass to and from between the plates of the ozone generator.

The generation of ions as well as ozone is beneficial when using hydrogen peroxide as a reactant. The ozone reacts with hydrogen peroxide, generating a number of radical species as illustrated in the equations below, and the ions accelerate the process and provide additional pathways for the generation of radicals.

$$H_2O_2 \rightarrow HO_2^- + H^+$$

$$O_3 + HO_2^- \rightarrow \cdot OH + O_2^{-\cdot} + O_2$$

$$O_3 + O_2^{-\cdot} \rightarrow O_3^{-\cdot} + O_2$$

$$O_3^{-\cdot} + H^+ \rightarrow HO_3 \cdot$$

$$HO_3 \cdot \rightarrow \cdot OH + O_2$$

The reaction of hydrogen peroxide with ozone is slow, but that of its anion, $HO_2^-$ is fast, and produces hydroxyl radicals. Another product of the reaction is $O_2^{-\cdot}$ radical, which also reacts with ozone to produce $O_3^{-\cdot}$. $O_3^{-\cdot}$ reacts with $H^+$ to produce $HO_3 \cdot$, which then dissociates into a hydroxyl radical and oxygen.

So a chain reaction is set up, and the yield of hydroxyl radicals is higher for a given amount of ozone than when using an olefin as the reactant.

As the amount of ozone required is very low, it is desirable to produce ions at the lowest possible voltage level with the ozone generator. This keeps the production of ozone low and minimizes the production of any undesirable nitric oxide. In order to achieve this, one of the electrodes within the plasma ion generator comprises a plurality of sharp spikes. The sharp spikes produce a large potential gradient within the ozone generator increasing the likelihood of ionization for a given applied voltage. The plasma ion generator is also configured to produce negative ions, again to keep ozone production within desirable levels.

The cartridge 905 includes electrical contact 945 for connecting to power supply in the base unit 900. The cartridge 905 also includes a transformer (not shown) in order to convert a 12V DC supply from the base unit to the necessary voltage for the ozone generator 935. The base unit includes a power supply socket 950 for connection to a power supply, typically a 12V DC supply adapted from the mains. The power socket 950 is electrically connected to contacts on the base unit that interface with the contacts 945 on the cartridge.

The air flow paths with in the apparatus shown in FIG. 9 are similar to that shown in FIG. 3, and are illustrated by the arrows in FIG. 9. The base unit includes a fan 955 which draws air in through an air inlet in the base of the base unit up into a narrowing air conduit 960. Air drawn in by the fan is accelerated as the conduit 960 narrows. The accelerated air flow then passes the ozone generator 935 in the cartridge, where ozone and ions are generated, and into mixing chamber 975 formed in the base unit. As in the embodiment of FIG. 3, the flow of air through conduit 960, past partition 970, draws air in through inlet 965 and over the wick 915 containing the hydrogen peroxide. The hydrogen peroxide rich air then exits into mixing chamber 975 where it mixes with and reacts with the ozone and ions from conduit 960 to form hydroxyl radicals, as previously described. The hydroxyl radicals then leave the mixing chamber through dispensing outlet 980.

As with embodiment shown in FIG. 3, the apparatus of FIG. 9 may be designed for different airflow. For example, the fan may be provided in the conduit with the wick and the internal geometry of the base unit and cartridge configured to use the Venturi effect to suck air past the ozone generator. Alternatively, the ozone generator and hydrogen peroxide supply may be placed in the same conduit, one after the other in the direction of air flow, or substantially opposite each other within the same conduit.

The apparatus shown in FIG. 9 also allows for the use of an optional scent supply, provided in a cartridge 990. Some of the air passing through conduit 960 is passed through cartridge 990 (as illustrated by the arrow in FIG. 9), introducing a scented chemical or chemicals into the environment.

The embodiment shown in FIGS. 9 and 10a and 10b, include an ozone generator that also ionizes air. However, it is possible to include a further or separate ionizer within or adjacent the air flow path through the apparatus. This is particularly useful if the ozone supply does not act as an ionizer. A possible position for a separate ionizer 985 is shown in dotted outline in FIG. 9. The ionizer may be any suitable type of negative ion generator. The ionizer may be placed anywhere along the air flow path in order to introduce ions into the air flow prior to dispensing outlet 980, and may be positioned within the base unit or within the cartridge.

The invention claimed is:

1. A consumable cartridge adapted for use with a base unit, the base unit and consumable cartridge together forming a hydroxyl radical generating apparatus, the base unit comprising a means for providing electrical power to the consumable cartridge and a means for driving air through the apparatus, the consumable cartridge comprising:
   a reactant supply comprising a supply of a substance that reacts with ozone to produce hydroxyl radicals, and
   an ozone supply comprising an ozone generator;
   wherein the ozone supply is fixed to the reactant supply.

2. A consumable cartridge according to claim 1, further comprising at least one electrical contact configured to allow connection of an external power supply to the ozone generator.

3. A consumable cartridge according to claim 1, further comprising an external housing, the reactant supply and the ozone supply being positioned within the external housing, wherein the electrical contact is accessible from an exterior of the housing.

4. A consumable cartridge according to claim 1, wherein the ozone generator is an electrically powered ozone generator.

5. A consumable cartridge according to claim 1, further comprising a transformer connected to the ozone generator.

6. A consumable cartridge according to claim 1, wherein the cartridge defines a first air inlet and a first outlet, wherein the first outlet is in fluid communication with the reactant supply and the first inlet; and
   wherein the cartridge defines a second air inlet and a second outlet, wherein the second outlet is in fluid communication with the ozone generator and the second air inlet.

7. A consumable cartridge according to claim 6, wherein the first outlet is positioned adjacent the second outlet, and the cartridge is configured so that air flow through one of the first outlet and the second outlet draws air through the other of the first outlet and the second outlet.

8. A consumable cartridge according to claim 6, further comprising a mixing chamber having a dispensing opening, the mixing chamber in fluid communication with both the first outlet and the second outlet, and configured to ensure a substantially complete reaction of vapors from the reactant supply with ozone from the ozone supply before release to the user environment through the dispensing opening.

9. A consumable cartridge according to claim 1, wherein the reactant supply is a supply of olefin or hydrogen peroxide.

10. A consumable cartridge according to claim 1, comprising an ion generator.

11. A consumable cartridge according to claim 10, wherein the ozone generator functions as the ion generator.

12. A base unit for producing hydroxyl radicals, the base unit suitable for use with a consumable cartridge in accordance with claim 1, comprising a means for connection with a power supply, a base unit air inlet, a means for moving air through the consumable cartridge, and a socket configured to receive the consumable cartridge, the socket including electrical contacts suitable for supplying electrical power from the means for connection with a power supply to the consumable cartridge.

13. A base unit according to claim 12, comprising a base unit air conduit between the base unit air inlet and either an air inlet on the consumable cartridge, wherein the base unit air inlet conduit narrows between the base unit air inlet and an air inlet on the consumable cartridge.

14. A base unit according to claim 12, further comprising an ion generator.

15. An apparatus for generating hydroxyl radicals comprising:
   a base unit; and
   a consumable cartridge, the base unit comprising a means for providing electrical power to the consumable cartridge, and a means for driving air through the apparatus.

16. An apparatus for generating hydroxyl radicals according to claim 15, wherein the base unit comprises a transformer for transforming an external supply voltage to a voltage suitable for the ozone generator in the consumable cartridge.

17. An apparatus for generating hydroxyl radicals according to claim 15, the base unit comprising a mixing chamber in fluid communication with an outlet of the reactant supply and an outlet of the ozone supply, the mixing chamber further comprising a dispensing outlet.

18. An apparatus for generating hydroxyl radicals according to claim 15, the base unit comprising a base unit air inlet and base unit air conduit between the base unit air inlet and an air inlet on the consumable cartridge, wherein the inlet conduit narrows between the base unit air inlet and the air inlet on the consumable cartridge.

19. An apparatus according to claim 15, comprising a first air inlet and a first air outlet, wherein the first outlet is in fluid communication with the reactant in the reactant supply and the first inlet; and
   a second air inlet and a second air outlet, wherein the second outlet is in fluid communication with the ozone generator and the second air inlet;
   wherein the first outlet is positioned adjacent the second outlet, and the apparatus is configured so that air flow through one of the first outlet and the second outlet draws air through the other of the first outlet and the second outlet.

20. An apparatus according to claim 15, comprising an ion generator in the base unit.

* * * * *